United States Patent [19]

Eveleens et al.

[11] 4,310,689
[45] Jan. 12, 1982

[54] PROCESS FOR THE PREPARATION OF OPTICALLY ACTIVE 2-PHENOXY PROPIONIC ACIDS AND HERBICIDAL PREPARATIONS CONTAINING SUCH ACIDS

[75] Inventors: Willem Eveleens, Hengelo; Johannes Spaans, Oldenzaal; Hendrik G. Wissink, Goor, all of Netherlands

[73] Assignee: Akzo N.V., Arnhem, Netherlands

[21] Appl. No.: 77,147

[22] Filed: Sep. 19, 1979

[30] Foreign Application Priority Data

Sep. 19, 1978 [NL] Netherlands ................. 7809514

[51] Int. Cl.$^3$ ............................................. C07C 59/48
[52] U.S. Cl. .................................. 562/472; 562/471; 71/116
[58] Field of Search ................... 71/116; 562/471, 472

[56] References Cited

U.S. PATENT DOCUMENTS 2,723,993 11/1955 Richardson .................. 562/472
4,013,451 3/1977 Poignant et al. .............. 71/116

FOREIGN PATENT DOCUMENTS 1114040 of 0000 United Kingdom.

Primary Examiner—Catherine L. Mills
Attorney, Agent, or Firm—Stevens, Davis, Miller & Mosher

[57] ABSTRACT

A process is provided for making D-2-phenoxy propionic acid by condensing in water an alkali metal salt of 2-chloropropionic acid which is dextro-rotatory in water with an alkali metal phenoxide of a halogen or methyl substituted phenol. The overall amount of water in the condensation mixture is not more than about 8 moles water per mole of said alkali metal salt of 2-chloropropionic acid in order to selectively produce the dextro-rotatory optical isomer.

2 Claims, No Drawings

PROCESS FOR THE PREPARATION OF OPTICALLY ACTIVE 2-PHENOXY PROPIONIC ACIDS AND HERBICIDAL PREPARATIONS CONTAINING SUCH ACIDS

This invention relates to a process for the preparation in water of a D-2-phenoxy propionic acid of the general formula

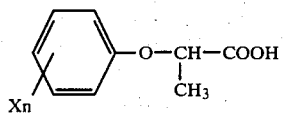
I.

where X represents a halogen atom and/or a methyl group and n is an integer of from 1 to 5, by condensing an alkali metal salt of 2-chloropropionic acid which is dextro-rotatory with an alkali metal phenoxide of a phenol of the general formula

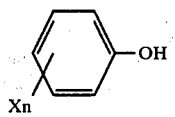
II.

with X and n having the same meaning as in formula I above.

A process of this general type is described in British Pat. No. 1,114,040. This known process, however, although it offers the important advantage of selective formation of the desired optical isomer with its herbicidal effect, has the disadvantage that the condensation reaction must be carried out in an organic solvent, such as toluene or xylene. This complicates carrying out the process industrially and provisions must be made for recovering the solvent. Moreover, the use of such solvents introduces environmental problems.

It is therefore an object of this invention to provide a process for condensing an alkali metal salt of 2-chloropropionic acid which is dextro-rotatory with an alkali metal phenoxide of a phenol to produce a D-2-phenoxy propionic acid having formula I above which is devoid of the foregoing disadvantages. Another object of the invention is to provide a process for condensing in an aqueous medium an alkali metal salt of 2-chloropropionic acid which is dextro-rotatory with an alkali metal phenoxide of a phenol of formula II above to prepare a compound having herbicidal properties of formula I, above.

The foregoing objects and others are accomplished in accordance with this invention, generally speaking, by providing a process for condensing in an aqueous medium an alkali metal salt of 2-chloropropionic acid which is dextro-rotatory in water and an alkali metal phenoxide of a phenol of formula II, above, under conditions which selectively produce D-2-phenoxy propionic acid which has herbicidal properties.

It has now been found that selective formation of the desired optical isomer can be effected in an aqueous medium, instead of an organic solvent, provided that the water content of the reaction mixture is kept sufficiently low. According to the invention the condensation is carried out in an aqueous medium in such a way that the overall amount of water in the reaction mixture is not more than about 8 moles per mole of alkali metal salt of 2-chloropropionic acid.

From the results of experiments it appears that in large amounts of water the condensation is as a rule not very selective and generally yields a racemic product. The selectivity, however, increases as the amount of water decreases, so that the end product contains more of the desired D-2-phenoxy propionic acid as the amount of water is decreased.

For practical reasons the resulting 2-phenoxy propionic acid product must contain more than about 85% of the active D-optical isomer for the preparation to be commercially attractive.

By limiting the water content per mole of 2-chloropropionic acid salt in the reaction mixture to not more than 8 moles of water, the product obtained will normally satisfy that condition and often times contains at least about 89% of the active D-isomer.

It is preferred to conduct the reaction in an aqueous medium containing some water but less than 3 moles of water per mole of 2-chloropropionic acid salt. This preferred process produces a phenoxy product of which on an average about 93% or more is the D-isomer.

The reaction cannot, of course, be carried out water-free and the lower limit of the amount of water used is determined by the manageability of the reaction mixture. Whether in the presence of little water the reaction mixture is still in solution or in the form of a slurry is partly dependent on the temperature. The reaction is usually carried out at an elevated temperature, and preferably at 80° C. or higher. As disclosed in the British Pat. No. 1,114,040, the optically active starting material, namely the dextro-rotatory alkali metal salt of 2-chloropropionic acid, is obtained by hydrolysis of the laevo-rotatory methyl ester of the propionic acid. This hydrolysis may be carried out in situ or separately. The ester is preferably hydrolyzed separately and the resulting propionic salt, which may be purified with methanol and dried, is added to the phenoxide, with due observation of the maximum permissible amount of water in the reaction mixture. By this route the process also may very well be carried out continuously. This invention is further described in the following examples.

EXAMPLE I

In five experiments D-2-(2-methyl 4-chlorophenoxy) propionic acid was prepared with various water contents in the reaction mixture. In the first four experiments, the following procedure was followed:

To a mixture of 122.5 g of L-2-chloropropionic methyl ester (actual $\alpha_D^{20} = -25.2°$) and 8 g of methanol, 133 g. of a 33% aqueous sodium hydroxide solution were added over a period of 40 minutes, with stirring and at a temperature below 40° C.

Subsequently, over a period of 60 minutes the resulting mixture was added, with stirring, to a mixture of 143 g of 2-methyl 4-chlorophenol, 38 g of sodium hydroxide and x g of water, with the temperature being kept at 90° C. The total mixture was then stirried for 1 more hour at 90° C.

The amount of x was determined by adding the sodium hydroxide as a 24%, 50% and 60% aqueous solution, respectively in Experiments 1 to 4.

Next, the reaction mixture was neutralized with hydrochloric acid to pH=7 and subsequently extracted three times with 50 ml of xylene to remove the excess chlorocresol.

The resulting aqueous solution was acidified with hydrochloric acid to pH=4, which was attended with the separation of an oily phase. This oil was extracted with ether, after which the extract was freed from ether by evaporation and dried to a constant weight.

In Experiment 5 the following procediure was used.

To a mixture of 122.5 g of L-2-chloropropionic methyl ester and 8 g of methanol there were added over a period of 40 minutes, with stirring and at a temperature below 40° C., 88 g of a 50%-sodium hydroxide solution. This mixture was subsequently purified and dried at 40° C. and 20 mm mercury pressure. The resulting product consisted of 130 g of a dry sodium salt of L-2-chloropropionic acid. Next, over a period of 60 minutes this dry salt was added, with stirring at at 90° C., to a mixture of 143 g of 2-methyl 4-chlorophenol, 38 g of sodium hydroxide and 20 g of water. The same procedure was followed as that described above with respect to Experiments 1-4.

The results of these experiments are summarized in the following table.

| Exp. No. | reaction mixture total water content (g) | molar ratio $H_2O$/propionate | Phenoxy endproduct $\alpha_D^{20}$ (in acetone) | % D-isomer |
| --- | --- | --- | --- | --- |
| 1 | 228 | 12.7 | + 18.9 | 83.6 |
| 2 | 196 | 10.9 | + 21.0 | 87.3 |
| 3 | 145 | 8.1 | + 22.1 | 89.2 |
| 4 | 132 | 7.3 | + 22.4 | 89.8 |
| 5 | 38 | 2.1 | + 25.0 | 94.4 |

The percentage D-isomer in the end product was calculated from the measured rotation $\alpha_D^{20}$ and the rotation $\alpha_D^{20} = +28.15°$ (10% in acetone) which holds for pure D-2-(2-methyl 4-chlorophenoxy) propionic acid. The table shows that the percentage of the desired D-isomer in the end product increases with decreasing molar ratio water/propionate in the reaction mixture, i.e. to such an extent that with a molar ratio of 8 water to 1 propionate or about 8-1, it exceeds 89%.

EXAMPLE II

In an additional five experiments the influence of water was tested in the preparation of D-2-(2,4-dichlorophenoxy) propionic acid. Experiments 7 and 8 were carried out using the same procedure as in Example I for Experiments 1-4. The saponified propionic ester was added to a caustic mixture of 163 g of 2,4-dichlorophenol, the amount of x being determined by employing 48% and 60% caustic solution, respectively in Experiments 7 and 8.

In the Experiments 6, 9 and 10 the procedure of Experiment 5 of Example I was followed using a different batch of the propionic ester starting material (actual $\alpha_D^{22} = -25.5°$).

The purified and dried sodium salt obtained from this material was added to a mixture of 163 g of 2,4-dichlorophenol, 38 g of sodium hydroxide and an amount of water equal to 220 g, 95 g and 31 g respectively in Experiments 6, 9 and 10.

The relevant experimental results are summarized in the next table.

| Exp. No. | reaction mixture total water content (g) | molar ratio $H_2O$ propionate | phenoxy endproduct $\alpha_D^{20}$ (in chloroform) | % D-isomer |
| --- | --- | --- | --- | --- |
| 6 | 238 | 13.2 | + 9.3 | 74.0 |
| 7 | 148 | 8.2 | + 12.9 | 83.7 |
| 8 | 132 | 7.3 | + 13.6 | 85.3 |
| 9 | 113 | 6.3 | + 13.9 | 86.1 |
| 10 | 49 | 2.7 | + 16.7 | 93.4 |

The percentage of D-isomer was calculated using $\alpha_D^{20} = +19.3°$ (in chloroform) for pure D-2-(2,4-dichlorophenoxy) propionic acid.

Again it is apparent from the table that at molar ratios below about 8 the percentage D-isomer in the endproduct exceeds the 85% level.

EXAMPLE III

Using the procedure of Experiments 1-4 of Example I a single preparation of D-2-(2-methylphenoxy) propionic acid was carried out. To this end the saponified propionic ester was added to a mixture of 108 g of 2-methyl phenol, 38 g of sodium hydroxide and 18 g of water.

Thus, in the reaction mixture the total water content amounted to 125 g, giving a molar ratio of water to propionate of 6.9 to 1. The rotation $\alpha_D^{20}$ of the endproduct was determined at +15.6° by measurement in chloroform. Using $\alpha_D^{20} = +18.2°$ (in chloroform) for pure D-2-(2-methylphenoxy) propionic acid the optical purity of the endproduct was calculated at 93% of the D-isomer.

The product of the process of the invention can be mixed with conventional additives to prepare a herbicide.

Although the invention is described in detail for the purpose of illustration it is to be understood that such detail is solely for that purpose and that variations can be made therein by those skilled in the art without departing from the spirit and scope of the invention except as it may be limited by the claims.

It is further to be understood that any suitable alkali metal salt or phenoxide of the propionic acid and phenol may be used, such as for example, the sodium, potassium or lithium salts and phenoxides.

What is claimed is:

1. In a process for making a D-2-phenoxy propionic acid having the formula

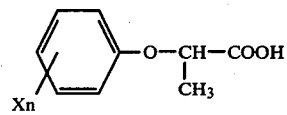

I.

wherein X is a halogen or methyl and n is an integer of 1 to 5 comprising reacting in water an alkali metal salt of 2-chloropropionic acid which is dextro-rotatory in water and an alkali metal phenoxide of a phenol having the formula

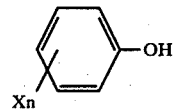

II.

wherein X and n have the same meanings as in formula I, the improvement which selectively produces the optical D-isomer and comprises limiting the overall water content of the reaction mixture to not more than about 8 moles of water per mole of said alkali metal salt, and maintaining the temperature of the reaction mixture at 80° C. or higher.

2. The process of claim 1, wherein the aqueous medium contains less than 3 moles of water per mole of said propionate.

* * * * *